(12) United States Patent
Lu et al.

(10) Patent No.: US 12,350,427 B2
(45) Date of Patent: Jul. 8, 2025

(54) VENTILATOR CONTROL METHOD AND VENTILATOR

(71) Applicant: GUANGDONG JIUCCO MEDICAL EQUIPMENT CO., LTD., Guangdong (CN)

(72) Inventors: Hua Lu, Guangdong (CN); Jiejing Lu, Guangdong (CN)

(73) Assignee: GUANGDONG JIUCCO MEDICAL EQUIPMENT CO., LTD., Guangdong (CN)

( * ) Notice: Subject to any disclaimer, the term of this patent is extended or adjusted under 35 U.S.C. 154(b) by 0 days.

(21) Appl. No.: 18/719,843

(22) PCT Filed: Sep. 6, 2023

(86) PCT No.: PCT/CN2023/117285
§ 371 (c)(1),
(2) Date: Jun. 14, 2024

(87) PCT Pub. No.: WO2024/131144
PCT Pub. Date: Jun. 27, 2024

(65) Prior Publication Data
US 2025/0108182 A1 Apr. 3, 2025

(30) Foreign Application Priority Data
Dec. 19, 2022 (CN) .......................... 202211629345.4

(51) Int. Cl.
*A61M 16/00* (2006.01)
*A61B 5/00* (2006.01)
(Continued)

(52) U.S. Cl.
CPC .......... *A61M 16/024* (2017.08); *A61B 5/0826* (2013.01); *A61B 5/4818* (2013.01);
(Continued)

(58) Field of Classification Search
CPC .......... A61M 16/0066; A61M 16/0069; A61M 16/024; A61M 16/06; A61M 16/105;
(Continued)

(56) References Cited

U.S. PATENT DOCUMENTS 5,458,137 A 10/1995 Axe et al.
12,213,775 B1 * 2/2025 Kayyali ............ A61M 16/0069
(Continued)

FOREIGN PATENT DOCUMENTS

CN 101448539 6/2009
CN 101888868 11/2010
(Continued)

OTHER PUBLICATIONS

"International Search Report (Form PCT/ISA/210) of PCT/CN2023/117285", mailed on Dec. 21, 2023, pp. 1-7.

*Primary Examiner* — Joseph D. Boecker
(74) *Attorney, Agent, or Firm* — JCIPRNET

(57) ABSTRACT

The present invention provides a ventilator control method a signal sensing module acquires a physiological signal feature of a user, a calibration and learning module learns the physiological signal feature of the user and outputs a drive signal after learning, and a main control module controls the operation efficiency of an air supply apparatus and opening and closing of a servo valve of a first servo valve box according to the drive signal, thus forming different operation modes. A ventilator performing the control method is provided. The present invention resolves the problem that the conventional ventilator is not compatible with the sleep apnea type of the user, and the problem that a single operation mode damages a patient's respiratory function. In the present invention, one ventilator is used to safely resolve various types of sleep apnea problems, greatly reducing costs of various types of ventilators purchased for the users.

7 Claims, 4 Drawing Sheets

(51) Int. Cl.
    *A61B 5/08*     (2006.01)
    *A61M 16/06*     (2006.01)
    *A61M 16/10*     (2006.01)
    *A61M 16/20*     (2006.01)
    *G16H 40/63*     (2018.01)
    *G16H 50/20*     (2018.01)
    *G16H 50/30*     (2018.01)

(52) U.S. Cl.
CPC ....... *A61B 5/4836* (2013.01); *A61M 16/0066* (2013.01); *A61M 16/0069* (2014.02); *A61M 16/06* (2013.01); *A61M 16/105* (2013.01); *A61M 16/204* (2014.02); *A61M 16/205* (2014.02); *G16H 40/63* (2018.01); *G16H 50/20* (2018.01); *G16H 50/30* (2018.01); *A61M 2016/0027* (2013.01); *A61M 2016/0033* (2013.01); *A61M 2205/3303* (2013.01); *A61M 2205/3334* (2013.01); *A61M 2205/50* (2013.01); *A61M 2205/75* (2013.01); *A61M 2230/005* (2013.01); *A61M 2230/10* (2013.01); *A61M 2230/40* (2013.01)

(58) Field of Classification Search
CPC .............. A61M 16/204; A61M 16/205; A61M 2016/0027; A61M 2016/0033; A61M 2205/3303; A61M 2205/3344; A61M 2230/005; A61M 2230/10; A61M 2230/40; G16H 50/20; G16H 50/30; A61B 5/0826; A61B 5/4818; A61B 5/4836

See application file for complete search history.

(56) References Cited

U.S. PATENT DOCUMENTS

| | | | |
|---|---|---|---|
| 2002/0023644 | A1* | 2/2002 | Berthon-Jones ....... A61B 5/085 128/204.22 |
| 2006/0037615 | A1* | 2/2006 | Wilkinson ............ A61B 5/085 128/204.23 |
| 2016/0074606 | A1 | 3/2016 | Whiting et al. |
| 2023/0190140 | A1* | 6/2023 | Tiron ..................... A61B 5/746 600/534 |

FOREIGN PATENT DOCUMENTS

| | | |
|---|---|---|
| CN | 101982204 | 3/2011 |
| CN | 106110456 | 11/2016 |
| CN | 107997764 | 5/2018 |
| CN | 115607786 | 1/2023 |
| WO | 9014121 | 11/1990 |

* cited by examiner

VENTILATOR CONTROL METHOD AND VENTILATOR

CROSS-REFERENCE TO RELATED APPLICATION

This application is a 371 of international application of PCT application serial no. PCT/CN2023/117285, filed on Sep. 6, 2023 which claims the priority benefit of China application no. 202211629345.4, filed on Dec. 19, 2022. The entirety of each of the above-mentioned patent applications is hereby incorporated by reference herein and made a part of this specification.

TECHNICAL FIELD

The present invention relates to the field of medical devices, and in particular to, a ventilator control method and a ventilator.

BACKGROUND

For various reasons, some people during sleep always experience a hypopnea state, which means that the air in mouth and nose flows at a speed lower than 50% of the normal airflow speed, without complete cessation.

Sleep apnea is much worse than hypopnea. There are approximately 100 million patients with sleep apnea in China. Some of them remain unaware about they have such illness and are untreated for several years, thus suffering from issues such as lack of concentration, high blood pressure, hypoxemia, and choking or suffocation due to airway closure at the middle of the night. Sleep apnea is a sleep disorder characterized by the cessation of breathing during sleep, and mainly includes three types: obstructive sleep apnea, central sleep apnea, and mixed sleep apnea. Obstructive sleep apnea refers to the absence of airflow through the nose and mouth while chest and abdominal respiration still exist. Central sleep apnea refers to the cessation of both nasal and oral airflow as well as chest and abdominal respiration. Mixed sleep apnea is a condition in which both obstructive sleep apnea and central sleep apnea occur simultaneously during a single breathing cessation.

Ventilators, by artificially supplementing or replacing spontaneous ventilation, have become indispensable devices for emergency medical care and life support in clinical studies. They are widely used in fields such as emergency medical care, anesthesia, ICU, and respiratory therapy. The ventilators can further be employed to address issues related to hypopnea and sleep apnea.

Currently, obstructive sleep apnea is typically treated using non-invasive continuous positive airway pressure (cpap) or automatic cpap (autocpap) machines. Central sleep apnea and mixed sleep apnea are often treated with bilevel positive airway pressure (bipap) machines.

The cpap machine only continuously delivers a constant pressure, and when the patient exhales, this continuous delivery of the constant pressure can make the patient feel suffocated. In addition, a long-term constant-pressure impact is likely to lead to issues such as airway barotrauma, localized fatigue of respiratory muscles, and even the occurrence of carbon deposits in respiratory muscle tissues. For sleep apnea not caused by only an obstructive issue, such as central or mixed apnea types, the bipap or auto-bipap machine is typically chosen. With each inhalation and exhalation, it delivers two different pressures. However, both bipap and auto-bipap machines not only cost a lot, but, after used for a long time, are likely to cause "lazy lung", that is, ventilator dependence. Therefore, the conventional ventilators are likely to damage the user's respiratory function.

The related literature may have also mentioned smart ventilators, but they are smart in that a sensor collects respiration-related information and provides it for a doctor to observe and diagnose respiratory pauses, and cannot be controlled smartly.

More importantly, many sleep apnea patients experience central, mixed, and obstructive sleep apnea symptoms simultaneously. However, currently, there has been no ventilator available to safely address various types of sleep apnea problems.

SUMMARY

To overcome the defects of the conventional ventilator control method, the present invention provides a ventilator control method. With this method used, not only the breathing state of a sleep apnea patient can be identified, but a control method can be provided based on the breathing state, such that one machine can safely resolve various types of sleep apnea problems.

Another objective of the present invention is to provide a ventilator performing the control method.

To resolve the foregoing technical problems, the present invention uses the following technical solution:

A ventilator control method is provided, where a physiological signal feature of a user is detected and acquired in real time, a current respiration type of the user is identified based on the physiological signal feature, when the respiration type is identified as a central sleep apnea type or a mixed sleep apnea type, a ventilator is controlled to provide a continuous-positive-airway-pressure ventilation-system operation mode for the user, and when the respiration type is identified as an obstructive sleep apnea type, a hypopnea type, or a spontaneous respiration type, the ventilator is controlled to provide a pulse operation mode for the user, where the pulse operation mode is to supply air when the user inhales and to control, when the user exhales, the ventilator to exhaust the supplied air, so as not to supply air to the user, thus supplying air in a pulse manner.

The ventilator control method includes the following steps:

S1: acquiring, by a signal sensing module, the physiological signal feature of the user in real time;

S2: identifying, by a main control module, the current respiration type of the user according to the physiological signal feature, where the respiration type includes the central sleep apnea type, the mixed sleep apnea type, the obstructive sleep apnea type, the hypopnea type, and the spontaneous respiration type; and if the current respiration type of the user is the central sleep apnea type or the mixed sleep apnea type, step S3 is performed, and if the current respiration type of the user is the obstructive sleep apnea type, the hypopnea type, or the spontaneous respiration type, step S4 is performed;

S3: controlling, by the main control module, an air supply apparatus to operate at full power and controlling a first servo valve to close, and returning to step S1;

S4: learning, by a calibration and learning module, the physiological signal feature acquired in step S1, to obtain a drive signal;

S5: controlling, by the main control module, an open-close cycle of the first servo valve according to the drive signal and controlling the air supply apparatus to operate at preset power; and S6: completing execution.

Preferably, in the ventilator control method, the power of the air supply apparatus is preset using any one of the following methods:

a first method: determining a ventilation pressure baseline suitable for the user through pressure titration, and presetting the power of the air supply apparatus based on the ventilation pressure baseline; and a second method: generating BMIs of the user based on height and weight inputted, each BMI being preset with corresponding power, and presetting the power of the air supply apparatus based on the power corresponding to the BMI of the user.

The present invention further provides a ventilator, including the air supply apparatus, a first servo valve box, a respiratory mask, the signal sensing module, the main control module, and the calibration and learning module; where the air supply apparatus is connected to the first servo valve box via tubing, and the first servo valve box is connected to the respiratory mask via tubing; the air supply apparatus, the first servo valve box, the signal sensing module, and the calibration and learning module are all electrically connected to the main control module; and the first servo valve box at least includes a first-valve-box main air passage, a first-valve-box branch air passage, and a first servo valve, and the first servo valve is disposed at an exhalation port of the first-valve-box branch air passage; where the air supply apparatus is configured to filter air to obtain purified air and convey the purified air along an air passage;

the first servo valve box is configured to receive a signal sent by the main control module and control the first servo valve to open and close;

the respiratory mask is configured to cover the nose or the mouth and nose of the user and provided with an exhaust hole for air exhaustion;

the signal sensing module is configured to acquire the physiological signal feature of the user and feed back the physiological signal feature to the main control module;

the main control module is configured to receive and send a signal and identify and process the signal; and the calibration and learning module is configured to learn the physiological signal feature of the user and output the drive signal to the main control module after learning, and the main control module controls the open-close cycle of the first servo valve according to the drive signal and controls the air supply apparatus to operate at the preset power.

In the foregoing solution, the signal sensing module acquires the physiological signal feature of the user, the calibration and learning module learns the physiological signal feature of the user and outputs the drive signal after learning, and the main control module controls the open-close cycle of the first servo valve according to the drive signal and controls the air supply apparatus to operate at the preset power. This avoids damage to the user's respiratory function, thus preventing the "lazy lung" phenomenon.

Preferably, the physiological signal feature includes a sleep signal feature and a respiration signal feature.

Preferably, the first servo valve box is provided with an inhalation port, a main exhalation port, and a branch exhalation port that form a three-port structure; where the inhalation port of the first servo valve box is connected to an exhalation port of the air supply apparatus via tubing, the main exhalation port of the first servo valve box is connected to an inhalation port of the respiratory mask via tubing, and the branch exhalation port of the first servo valve box is left open or connected to an inhalation port of the air supply apparatus via tubing.

Preferably, the air supply apparatus includes a fan and an air filter box or an oxygen-air mixer. The air filter box or oxygen-air mixer is configured to adjust the oxygen concentration of the supplied air. An exhalation port of the fan is connected to the inhalation port of the first servo valve box via tubing, and an inhalation port of the fan is connected to an exhalation port of the air filter box via tubing; and the fan is electrically connected to the main control module.

Preferably, when the branch exhalation port of the first servo valve box is connected to the inhalation port of the air supply apparatus via tubing, the air supply apparatus further includes a second servo valve box, where the second servo valve box is provided with a main inhalation port, a branch inhalation port, and an exhalation port that form a three-port structure; where the exhalation port of the second servo valve box is connected to an inhalation port of the air filter box via tubing, and the branch inhalation port of the second servo valve box is connected to the branch exhalation port of the first servo valve box via tubing; and the second servo valve box is electrically connected to the main control module; and the second servo valve box is configured to receive a signal sent by the main control module and control the second servo valve to open and close.

Preferably, the signal sensing module includes an air flow sensor and a signal amplification module, where the air flow sensor is electrically connected to the signal amplification module, and the signal amplification module is electrically connected to the main control module.

The air flow sensor is close to an inhalation port of the respiratory mask and configured to acquire an air flow change as the respiration signal feature of the user and send the respiration signal feature to the signal amplification module.

The signal amplification module is configured to amplify the signal sent by the sensor and send the amplified signal to the main control module.

Preferably, the signal sensing module further comprises a pressure sensor, the pressure sensor being electrically connected to the signal amplification module.

The pressure sensor is configured to acquire fluctuations of the chest and abdominal area of the user as the respiration signal feature of the user, and send the sleep signal feature to the signal amplification module.

Preferably, the ventilator further includes an electroencephalogram sensor and an eye muscle electromyography sensor, where the electroencephalogram sensor and the eye muscle electromyography sensor are both electrically connected to the main control module.

The electroencephalogram sensor is configured to acquire an electroencephalogram signal of the user as a sleep signal feature of the user, and send the sleep signal feature to the signal amplification module.

The eye muscle electromyography sensor is configured to acquire an eye muscle electromyography signal of the user as a sleep signal feature of the user and send the sleep signal feature to the signal amplification module.

Compared with the related art, the technical solution of the present invention has the following beneficial effects:

The present invention provides a new ventilator control method, where with one ventilator used, the physiological signal feature of the user can be detected and acquired in real time, and a current respiration type of the user is identified based on the physiological signal feature. When the respiration type is identified as a central sleep apnea type or a mixed sleep apnea type, the ventilator is controlled to provide e a continuous-positive-airway-pressure ventilation-system operation mode for the user, and when the respiration type is identified as an obstructive sleep apnea type, a hypopnea type, or a spontaneous respiration type, the ventilator is controlled to provide a pulse operation mode for the user. The signal sensing module acquires the physiological signal feature of the user, the calibration and learning module learns the physiological signal feature of the user and outputs the drive signal after learning, and the main control module controls the open-close cycle of the first servo valve according to the drive signal and controls the air supply apparatus to operate at the preset power. This avoids damage to the user's respiratory function, thus preventing the "lazy lung" phenomenon.

Long-term research in the related art has summarized different sleep apnea types. A few studies have proposed that doctors use findings of relevant research to observe and diagnose the sleep apnea types of patients, but there has been no technical solution that is aimed to assist in breathing, where one ventilator resolves all sleep apnea types. The present invention overcomes the long-term technical dilemma in the related art where patients with different sleep apnea types need to use corresponding types of ventilators, but some of them each have various sleeps apnea types that always change, and resolves the problem that the conventional ventilator is incompatible with the sleep apnea type of the user, and also addresses the problem that a single operation mode damages the patient's respiratory function. Therefore, one ventilator is used to safely resolve various types of sleep apnea problems, greatly reducing costs of various types of ventilators purchased for the users.

Figure 1:
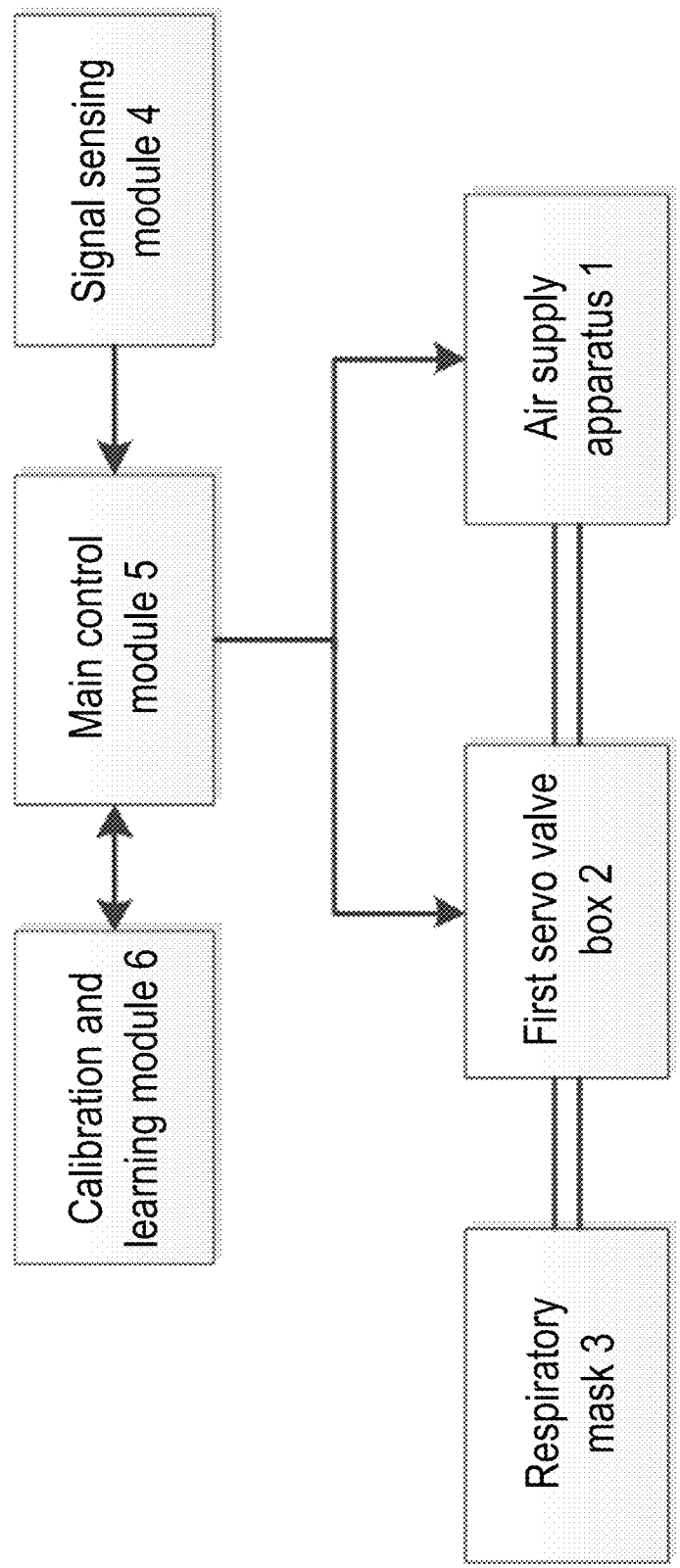
FIG. 1 is a schematic diagram of a module connection according to an embodiment of the present invention.

Numeral references are as follows: 1. air supply apparatus; 11. fan; 12. air filter box; 13. second servo valve box; 14. silencer; 2. first servo valve box; 3. respiratory mask; 4. signal sensing module; 41. air flow sensor; 42. signal amplification module; 43. pressure sensor; 44. electroencephalogram sensor; 45. eye muscle electromyography sensor; 5. main control module; and 6. calibration and learning module.

DETAILED DESCRIPTION OF EMBODIMENTS

Accompanying drawings are provided for illustrative purposes only and should not be construed as limiting the scope of this application.

To better illustrate the embodiments, some components in the drawings may be omitted, enlarged, or reduced, which does not necessarily represent the actual product dimensions.

It is understandable for those skilled in the art that some known structures and their descriptions in the drawings may be omitted.

The technical solution of the present invention is further described in detail with reference to the accompanying drawings and examples.

Embodiment 1

As shown in FIG. 1, a ventilator is provided, including an air supply apparatus 1, a first servo valve box 2, a respiratory mask 3, the signal sensing module 4, a main control module 5, and a calibration and learning module 6. The air supply apparatus 1 is connected to the first servo valve box 2 via tubing, and the first servo valve box 2 is connected to the respiratory mask 3 via tubing. The air supply apparatus 1, the first servo valve box 2, the signal sensing module 4, and the calibration and learning module 6 are all electrically connected to the main control module 5. The first servo valve box 2 at least includes a first-valve-box main air passage, a first-valve-box branch air passage, and a first servo valve, and the first servo valve is disposed at an exhalation port of the first-valve-box branch air passage.

The air supply apparatus 1 is configured to filter air to obtain purified air and convey the purified air along an air passage.

The first servo valve box 2 is configured to receive a signal sent by the main control module 5 and control the first servo valve to open and close.

The respiratory mask 3 is configured to cover the nose or the mouth and nose of the user and provided with an exhaust hole for air exhaustion.

The signal sensing module 4 is configured to acquire the physiological signal feature of the user and feed back the physiological signal feature to the main control module 5.

The main control module 5 is configured to receive and send a signal and identify and process the signal.

The calibration and learning module 6 is configured to learn the physiological signal feature of the user and output the drive signal to the main control module 5 after learning, and the main control module 5 controls the open-close cycle of the first servo valve according to the drive signal and controls the air supply apparatus 1 to operate at preset power.

During actual application, an FPGA calibration and learning module 6 is used to learn the physiological signal feature of the user through programming and output the corresponding drive signal.

During actual implementation, the respiratory mask 3 is used to cover the nose or nose and mouth of the user, and the signal sensing module 4 is correspondingly arranged according to its function. Then, the air supply apparatus 1 is started to draw in air outside, filter it to obtain purified air with breathable air quality, and deliver the purified air into the human airway along the air passage. Within one minute before the start of the normal operation (the duration can be adjusted depending on the actual case), the air supply apparatus 1 operates at 80% of the full power, the first servo valve closes, and the purified air enters the human airway along the main air passage. The signal sensing module 4 acquires the corresponding physiological signal feature and feeds back the feature to the main control module 5, the main control module 5 sends the physiological signal feature to the calibration and learning module 6 for study within this minute, and then a drive signal after study is obtained and sent to the main control module 5. The main control module 5 controls the operation efficiency of the air supply apparatus 1 according to the drive signal and the servo valve of the first servo valve box 2 to open or close until a new drive signal is received, allowing the ventilator to flexibly operate in the corresponding operation model, thus avoiding damage to the user' respiratory function and the "lazy lung" phenomenon.

Embodiment 2

Figure 2:
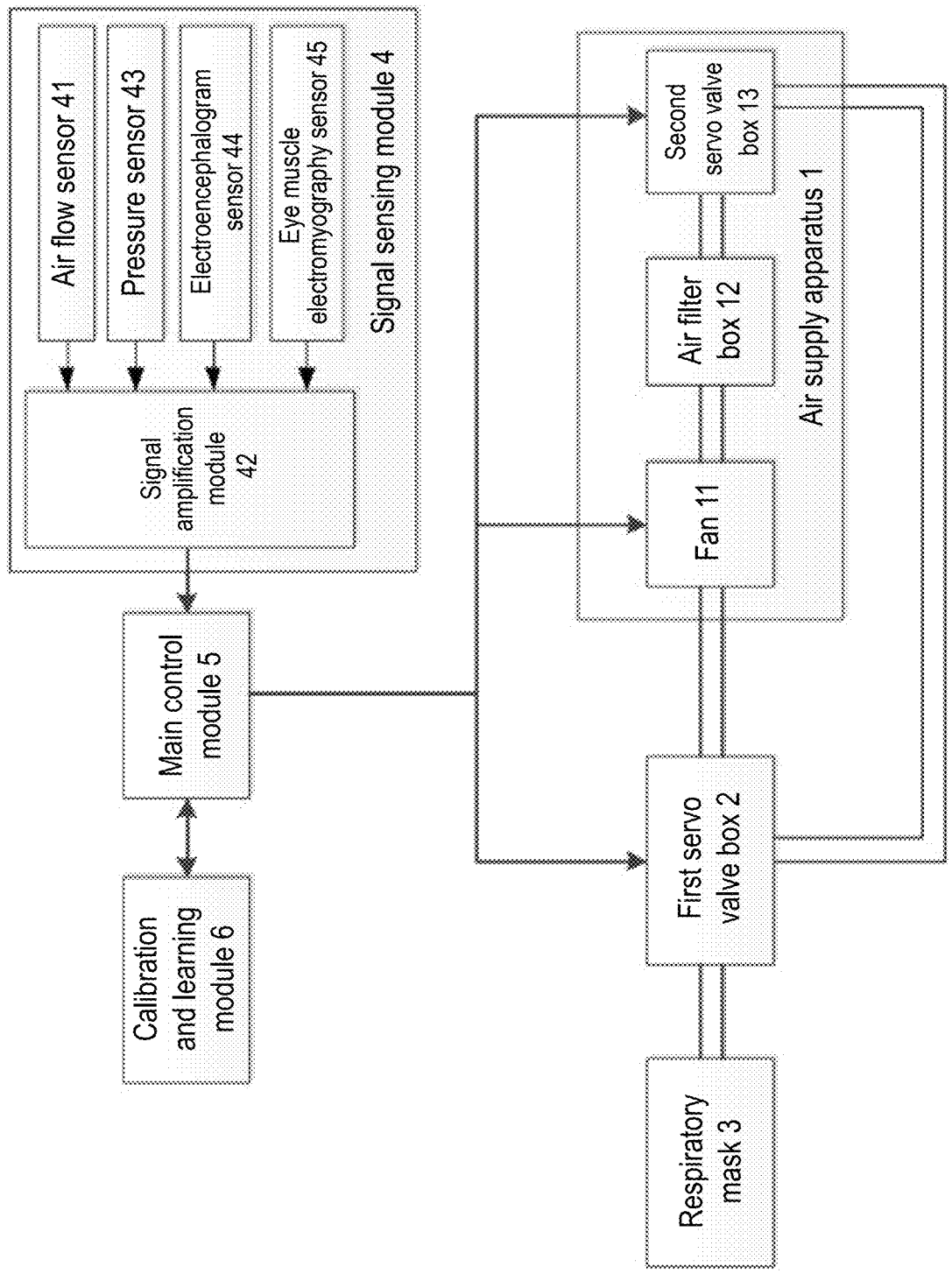
FIG. 2 is a schematic diagram of a module connection according to another embodiment of the present invention.

As shown in FIG. 2, a ventilator is provided, including an air supply apparatus 1, a first servo valve box 2, a respiratory mask 3, the signal sensing module 4, a main control module 5, and a calibration and learning module 6. The air supply apparatus 1 is connected to the first servo valve box 2 via tubing, and the first servo valve box 2 is connected to the respiratory mask 3 via tubing. The air supply apparatus 1, the first servo valve box 2, the signal sensing module 4, and the calibration and learning module 6 are all electrically connected to the main control module 5. The first servo valve box 2 at least includes a first-valve-box main air passage, a first-valve-box branch air passage, and a first servo valve, and the first servo valve is disposed at an exhalation port of the first-valve-box branch air passage.

The air supply apparatus 1 is configured to filter air to obtain purified air and convey the purified air along an air passage.

The first servo valve box 2 is configured to receive a signal sent by the main control module 5 and control the first servo valve to open and close.

The respiratory mask 3 is configured to cover the nose or the mouth and nose of the user and provided with an exhaust hole for air exhaustion.

The signal sensing module 4 is configured to acquire the physiological signal feature of the user and feed back the physiological signal feature to the main control module 5.

The main control module 5 is configured to receive and send a signal and identify and process the signal.

The calibration and learning module 6 is configured to learn the physiological signal feature of the user and output the drive signal to the main control module 5 after learning, and the main control module 5 controls the open-close cycle of the first servo valve according to the drive signal and controls the air supply apparatus 1 to operate at preset power.

More specifically, the physiological signal feature includes a sleep signal feature and a respiration signal feature.

More specifically, the signal sensing module 4 includes an air flow sensor 41 and a signal amplification module 42, where the air flow sensor 41 is electrically connected to the signal amplification module 42, and the signal amplification module 42 is electrically connected to the main control module 5.

The air flow sensor 41 is close to an inhalation port of the respiratory mask 3 and configured to acquire an air flow change as the respiration signal feature of the user and send the respiration signal feature to the signal amplification module 42.

The signal amplification module 42 is configured to amplify the signal sent by the sensor and send the amplified signal to the main control module 5.

More specifically, the signal sensing module 4 further includes a pressure sensor 43, the pressure sensor 43 being electrically connected to the signal amplification module 42.

The pressure sensor 43 is configured to acquire fluctuations of the chest and abdominal area of the user as the respiration signal feature of the user, and send the sleep signal feature to the signal amplification module 42.

More specifically, the pressure sensor 43 is a chest and abdomen sensing belt. The chest and abdomen sensing belt may be integrated or include a chest sensing belt and an abdomen sensing that are arranged separately.

Figure 3:
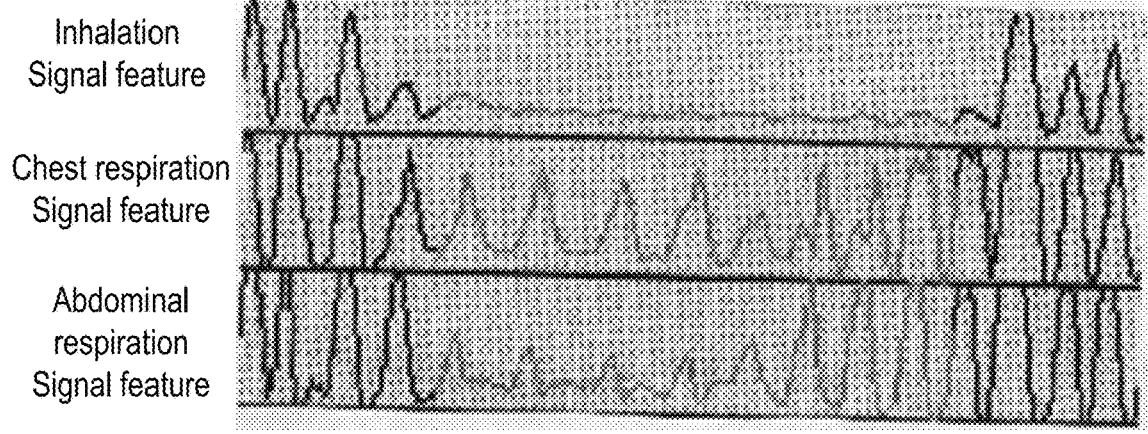
FIG. 3 is a schematic diagram of a respiration signal feature of obstructive sleep apnea according to the present invention.

During actual implementation, the respiratory mask 3 is used to cover the nose or nose and mouth of the user, and the chest and abdomen sensing belt is used to correspondingly surround the chest and abdomen of the user. The air supply apparatus 1 is started to draw in the air outside, filter it to obtain purified air with breathable air quality, and deliver the purified air into the human airway along the air passage. Within one minute before the start of the normal operation (the duration can be adjusted depending on the actual case), the air supply apparatus 1 operates at 80% of the full power, the first servo valve closes, and the purified air enters the human airway along the main air passage. The air flow sensor 41 acquires the air flow change in the main air passage to obtain an inhalation signal feature of the user, and the calibration and learning module 6 learns the inhalation signal feature within this minute. A drive signal is obtained after learning and sent to the main control module 5, and then the main control module 5 controls the open-close cycle of the first servo valve according to the drive signal and controls the air supply apparatus 1 to operate at preset power. Thereby, when the user inhales, the main control module 5 controls the first servo valve to close, and the purified air is delivered into the human airway along the air passage. When the user exhales, the main control module 5 controls the first servo valve to open, where the openness degree of the first servo valve can be preset according to the actual requirements. The air exhaled by the user directly confronts the air blown by the air supply apparatus 1, and all or most of the purified air is discharged directly through the first servo valve. The air exhaled by the user is discharged via the exhaust hole of the respiratory mask 3, allowing the user to breathe more smoothly. This is suitable in response to the obstructive sleep apnea, hypopnea, and spontaneous respiration, with the respiration signal feature of obstructive sleep apnea shown in FIG. 3. This is a pulse operation mode.

The fluctuations of the chest and abdomen of the user are acquired continuously in real time using the chest and abdomen sensing belt to obtain a chest respiration signal feature and an abdomen respiration signal feature of the user. Then, the main control module 5 combines the inhalation signal feature, the chest respiration signal feature, and the abdomen respiration signal feature for determination, such that a corresponding operation mode is executed.

Figure 4:
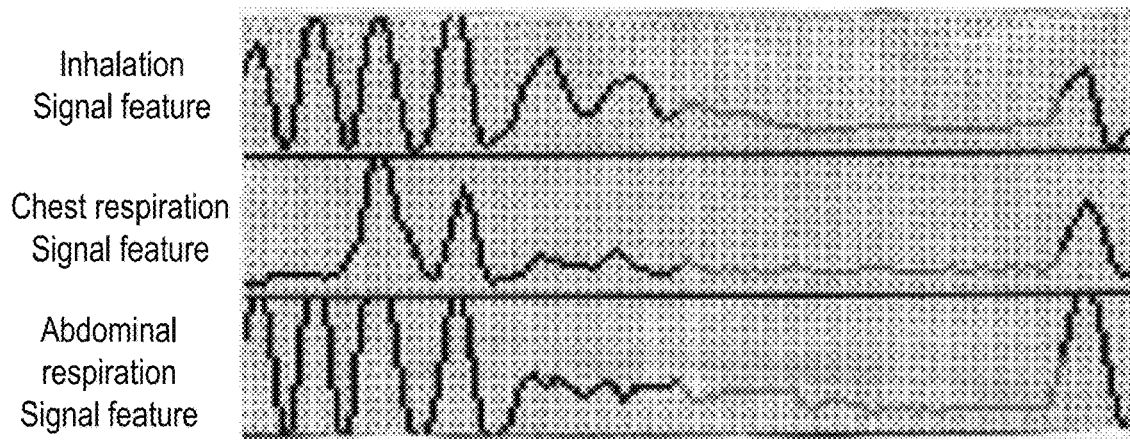
FIG. 4 is a schematic diagram of a respiration signal feature of central sleep apnea according to the present invention.

As shown in FIG. 4, when the inhalation signal feature weakens or disappears, and the chest respiration signal feature and the abdomen respiration signal feature both disappear, that is, when the user inhales less air or cannot inhale air, and the chest and the abdomen do not fluctuate, the main control module 5 controls the air supply apparatus 1 to operate at full power, and the first servo valve to close, so as to enter the continuous-positive-airway-pressure ventilation-system operation mode. The purified air is continuously delivered into the human airway along the air passage, presenting the user from accidents caused by the central sleep apnea. If the inhalation signal feature, the chest respiration signal feature, and the abdomen respiration signal feature restore normally, after the operation mode lasts for three minutes (the duration can be adjusted according to the actual case), the main control module 5 again controls the open-close cycle of the first servo valve according to the drive signal and controls the air supply apparatus 1 to operate at preset power.

If the normal restoration of the chest respiration signal feature or the abdomen respiration signal feature is not detected within three respiration cycles (the duration can be adjusted according to the actual case), an equipped alarm emits alert. The duration can be adjusted according to the actual case. Such operation mode is suitable in response to central sleep apnea.

Figure 5:
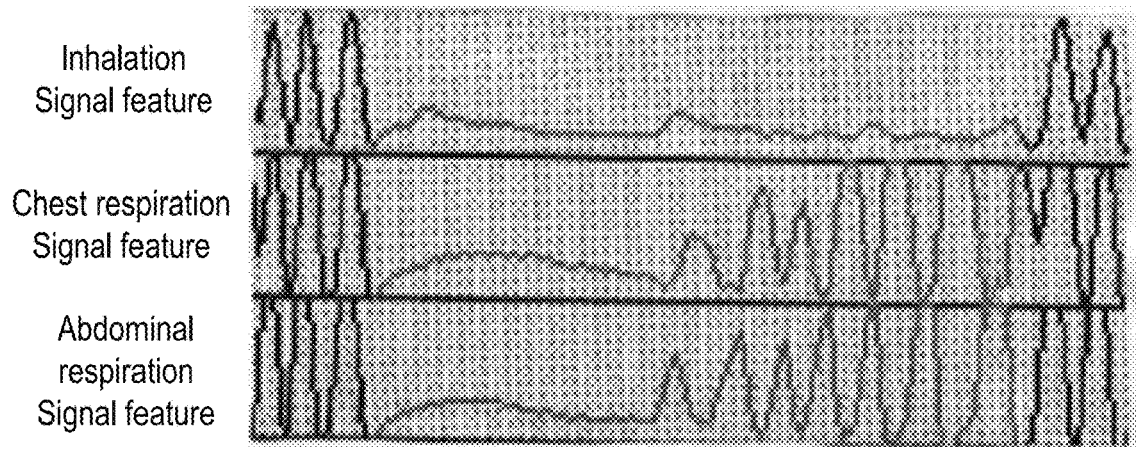
FIG. 5 is a schematic diagram of a respiration signal feature of mixed sleep apnea according to the present invention.

As shown in FIG. 5, when the inhalation signal feature weakens or disappears, and the chest respiration signal feature and the abdomen respiration signal feature disappear and restore but are weak, it is determined that mixed sleep apnea occurs. The main control module 5 controls the air supply apparatus 1 to operate at full power, and the first servo valve to close, so as to enter the continuous-positive-airway-pressure ventilation-system operation mode. The purified air is continuously delivered into the human airway along the air passage, presenting the user from accidents caused by the mixed sleep apnea. If the inhalation signal feature, the chest respiration signal feature, and the abdomen respiration signal feature restore normally, after the operation mode lasts for three minutes (the duration can be adjusted according to the actual case), the main control module 5 again controls the open-close cycle of the first servo valve according to the drive signal and controls the air supply apparatus 1 to operate at preset power.

If the normal restoration of the chest respiration signal feature or the abdomen respiration signal feature is not detected within three respiration cycles (the duration can be adjusted according to the actual case), an equipped alarm emits alert. The duration can be adjusted according to the actual case. Such operation mode is suitable in response to mixed sleep apnea.

Embodiment 3

A ventilator is provided, including an air supply apparatus 1, a first servo valve box 2, a respiratory mask 3, a signal sensing module 4, a main control module 5, and a calibration and learning module 6. The air supply apparatus 1 is connected to the first servo valve box 2 via tubing, and the first servo valve box 2 is connected to the respiratory mask 3 via tubing. The air supply apparatus 1, the first servo valve box 2, the signal sensing module 4, and the calibration and learning module 6 are all electrically connected to the main control module 5. The first servo valve box 2 at least includes a first-valve-box main air passage, a first-valve-box branch air passage, and a first servo valve, and the first servo valve is disposed at an exhalation port of the first-valve-box branch air passage.

The air supply apparatus 1 is configured to filter air to obtain purified air and convey the purified air along an air passage.

The first servo valve box 2 is configured to receive a signal sent by the main control module 5 and control the first servo valve to open and close.

The respiratory mask 3 is configured to cover the nose or the mouth and nose of the user and provided with an exhaust hole for air exhaustion.

The signal sensing module 4 is configured to acquire the physiological signal feature of the user and feed back the physiological signal feature to the main control module 5.

The main control module 5 is configured to receive and send a signal and identify and process the signal.

The calibration and learning module 6 is configured to learn the physiological signal feature of the user and output the drive signal to the main control module 5 after learning, and the main control module 5 controls the open-close cycle of the first servo valve according to the drive signal and controls the air supply apparatus 1 to operate at preset power.

More specifically, the ventilator further includes an electroencephalogram sensor 44 and an eye muscle electromyography sensor 45, where the electroencephalogram sensor 44 and the eye muscle electromyography sensor 45 are both electrically connected to the main control module 5.

The electroencephalogram sensor 44 is configured 1 to acquire an electroencephalogram signal of the user as a sleep signal feature of the user, and send the sleep signal feature to the signal amplification module 42.

The eye muscle electromyography sensor 45 is configured to acquire an eye muscle electromyography signal of the user as a sleep signal feature of the user and send the sleep signal feature to the signal amplification module 42.

During application, the sleep state and depth of the user are determined based on the electroencephalogram signal acquired by the electroencephalogram sensor 44, and the sleep cycle of the user is determined based on the eye muscle electromyography signal acquired by the eye muscle electromyography sensor 45, such that the main control module 5 can control the air supply apparatus 1 and the first servo valve based on the sleep state, depth, and cycle of the user, so as to adjust the air supply pressure, thus preventing high air supply pressure from affecting the sleep quality of the user, improving the sleep comfort.

Embodiment 4

A ventilator is provided, including an air supply apparatus 1, a first servo valve box 2, a respiratory mask 3, a signal sensing module 4, a main control module 5, and a calibration and learning module 6. The air supply apparatus 1 is connected to the first servo valve box 2 via tubing, and the first servo valve box 2 is connected to the respiratory mask 3 via tubing. The air supply apparatus 1, the first servo valve box 2, the signal sensing module 4, and the calibration and learning module 6 are all electrically connected to the main control module 5. The first servo valve box 2 at least includes a first-valve-box main air passage, a first-valve-box branch air passage, and a first servo valve, and the first servo valve is disposed at an exhalation port of the first-valve-box branch air passage.

The air supply apparatus 1 is configured to filter air to obtain purified air and convey the purified air along an air passage.

The first servo valve box 2 is configured to receive a signal sent by the main control module 5 and control the first servo valve to open and close.

The respiratory mask 3 is configured to cover the nose or the mouth and nose of the user and provided with an exhaust hole for air exhaustion.

The signal sensing module 4 is configured to acquire the physiological signal feature of the user and feed back the physiological signal feature to the main control module 5.

The main control module 5 is configured to receive and send a signal and identify and process the signal.

The calibration and learning module 6 is configured to learn the physiological signal feature of the user and output the drive signal to the main control module 5 after learning, and the main control module 5 controls the open-close cycle of the first servo valve according to the drive signal and controls the air supply apparatus 1 to operate at preset power.

More specifically, the first servo valve box 2 is provided with an inhalation port, a main exhalation port, and a branch exhalation port that form a three-port structure, where the inhalation port and the main exhalation port jointly form a first-valve-box main air passage, and the inhalation port and the branch exhalation port jointly form a first-valve-box branch air passage.

The inhalation port of the first servo valve box 2 is connected to an exhalation port of the air supply apparatus 1 via tubing, the main exhalation port of the first servo valve box 2 is connected to an inhalation port of the respiratory mask 3 via tubing, and the branch exhalation port of the first servo valve box 2 is left open or connected to an inhalation port of the air supply apparatus 1 via tubing.

More specifically, the air supply apparatus 1 includes a fan 11 and an air filter box 12; where an exhalation port of the fan 11 is connected to the inhalation port of the first servo valve box 2 via tubing, and an inhalation port of the fan 11 is connected to an exhalation port of the air filter box 12; and the fan 11 is electrically connected to the main control module 5.

During application, the air filter box 12 includes a coarse filter, a precision filter/plasma curtain/ultrapure water curtain, and the like.

More specifically, the branch exhalation port of the first servo valve box 2 is connected to the inhalation port of the air supply apparatus 1 via tubing, and the air supply apparatus 1 further includes a second servo valve box 13, where the second servo valve box 13 is provided with a main inhalation port, a branch inhalation port, and an exhalation port that form a three-port structure; and the second servo valve box 13 is electrically connected to the main control module 5.

An exhalation port of the second servo valve box 13 is connected to an inhalation port of the air filter box 12 via tubing, and the branch inhalation port of the second servo valve box 13 is connected to the branch exhalation port of the first servo valve box 2 via tubing.

The second servo valve box 13 is configured to receive a signal sent by the main control module 5 and control the second servo valve to open.

During specific implementation, the first servo valve and the second servo valve are opened and closed at the same time and their openness levels correspond to each other. When the first servo valve and the second servo valve open, a proportional return air passage is formed, such that the air exhaled by the user confronts the air blown by the fan 11, and the exhaled air is discharged via the exhaust hole of the respiratory mask 3. The purified air is discharged from the branch exhalation port of the first servo valve box 2 and delivered along the proportional return air passage, enters along the branch inhalation port of the second servo valve box 13, and is filtered again by the air filter box 12 and delivered, improving the air utilization efficiency and delivery speed. When the first servo valve is closed, purified air enters the user's airway under the fan's blowing force, with the user's inhalation action, and the airflow expands the obstructed airway. The main control module 5 controls the first servo valve to open or close according to the drive signal, to supply air to the user by simulating the pulse pattern.

More specifically, the air supply apparatus 1 further includes two silencers, which are respectively close to the inhalation port and the exhalation port of the fan 11, where the silencer is configured to reduce noise.

Embodiment 5

Figure 6:
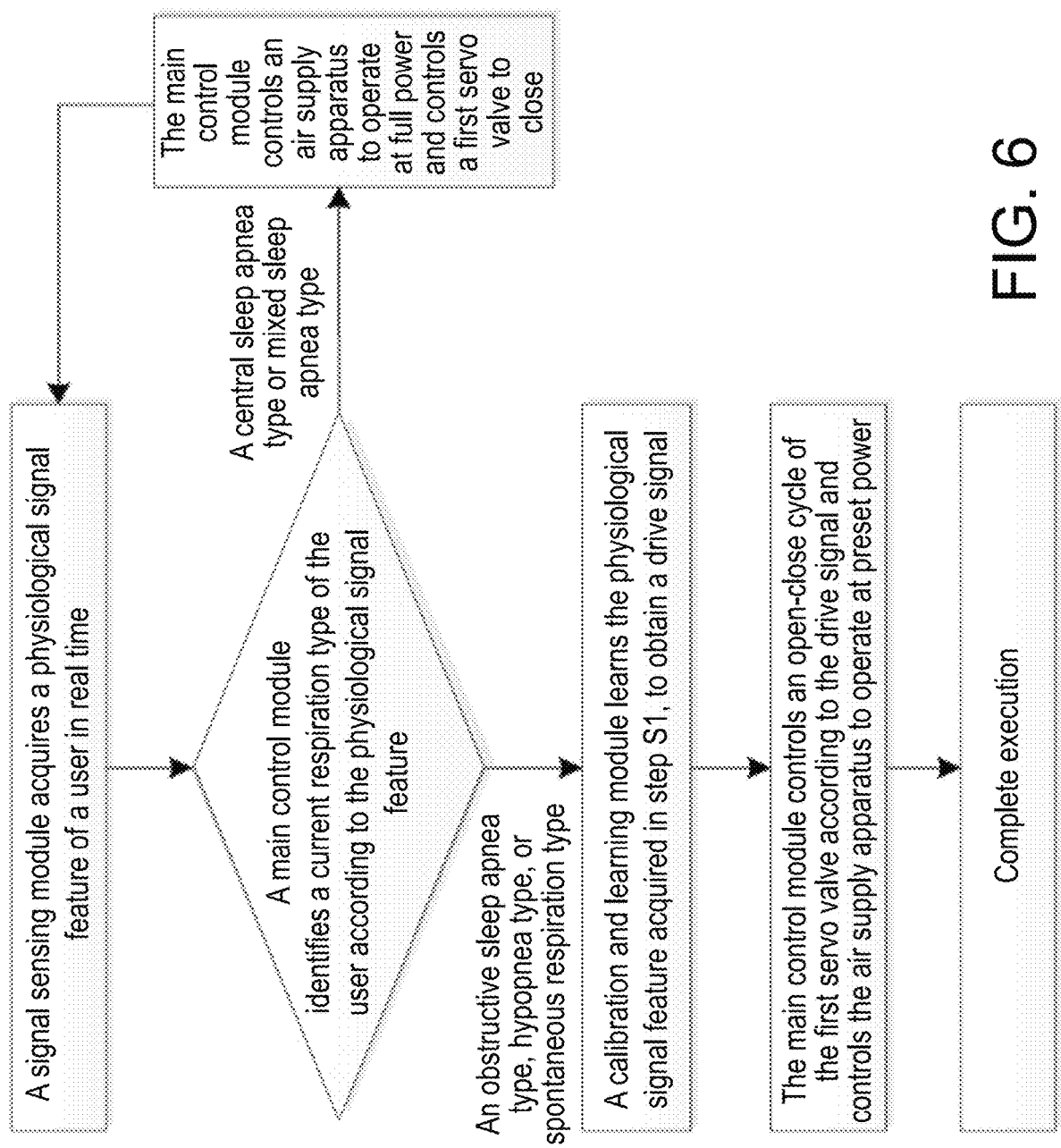
FIG. 6 is a flowchart of actual steps of a technical solution according to the present invention.

As shown in FIG. 6, a ventilator control method is implemented based on a ventilator, including the following steps:

S1: A signal sensing module 4 acquires a physiological signal feature of a user in real time.

S2: A main control module 5 identifies a current respiration type of the user according to the physiological signal feature.

The respiration type includes a central sleep apnea type, a mixed sleep apnea type, an obstructive sleep apnea type, a hypopnea type, and a spontaneous respiration type.

If the current respiration type of the user is the central sleep apnea type or the mixed sleep apnea type, step S3 is performed.

If the current respiration type of the user is the obstructive sleep apnea type, the hypopnea type, or the spontaneous respiration type, step S4 is performed.

During actual application, when the inhalation signal feature of the user weakens or disappears, and the chest respiration signal feature and the abdomen respiration signal feature disappear, that is, when the user inhales less air or cannot inhale air, and the chest and the abdomen don not fluctuate, the current respiration type of the user is determined as the central sleep apnea type.

When the inhalation signal feature of the user weakens or disappears, and the chest respiration signal feature and the abdomen respiration signal feature disappear and restore but are weak, that is, when the user inhales less air or cannot inhale air, and the chest and abdomen do not fluctuate for a period and then start to slightly fluctuate, the current respiration type of the user is determined as the mixed sleep apnea type.

When the inhalation signal feature of the user disappears, but the chest respiration signal feature or the abdomen respiration signal feature does not disappear, that is, when the user cannot inhale air, but the chest and the abdomen fluctuate, the current respiration type of the user is determined as the obstructive sleep apnea type.

Generally, the average of ten consecutive ventilation amounts acquired within the first minute (the duration can be adjusted based on the actual case) after start of the ventilator is taken as the normal ventilation amount, where the ventilation amount is acquired by the air flow sensor 41. The ventilation amount of the user is monitored in real time. When the inhalation signal feature occurs during monitoring, and the chest respiration signal feature or the abdomen respiration signal feature does not disappear, but the average of ten consecutive ventilation amounts is lower than 50% of the normal ventilation amount, that is, the user inhales but the average of ten consecutive ventilation amounts is reduced to be below 50% of the normal ventilation amounts, the current respiration type of the user is determined as the hypopnea type.

If the inhalation signal feature occurs, the chest respiration signal feature or the abdomen respiration signal feature does not disappear, and the average of any ten consecutive ventilation amounts of the user is not lower than 50% of the normal ventilation amount, the current respiration type of the user is determined as the spontaneous respiration type.

S3: The main control module 5 controls an air supply apparatus 1 to operate at full power and controls a first servo valve to close, and return to step S1.

S4: A calibration and learning module 6 learns the physiological signal feature acquired in step S1, to obtain a drive signal.

S5: The main control module 5 controls an open-close cycle of the first servo valve according to the drive signal and controls the air supply apparatus 1 to operate at preset power.

S6: Complete execution.

More specifically, the power of the air supply apparatus is preset according to any one of the following methods:

a first method: determining a ventilation pressure baseline suitable for the user through pressure titration, and presetting the power of the air supply apparatus based on the ventilation pressure baseline; and a second method: generating BMIs of the user based on height and weight inputted, each BMI being preset with corresponding power, and presetting the power of the air supply apparatus based on the power corresponding to the BMI of the user.

During the specific implementation, due to individual differences in respiratory strength and frequency, it is necessary to pre-determine the appropriate ventilation pressure baseline for the user through pressure titration. Consequently, the operation power of the air supply apparatus 1 is set based on the ventilation pressure baseline. The ventilation pressure baseline is not an absolute value; it can dynamically change within a small range. Therefore, in practice, the operation power of the air supply apparatus 1 may be set to multiple levels from which the main control module 5 selects an appropriate level based on different drive signals. Additionally, the appropriate power can be selected directly based on the user's BMIs. For example, of the BMIs, a range of [25, 30) is defined as a first level S, a range of [30, 35) is defined as a second level M, and a range of [35, 40) is defined as a third level L. By analog, each level corresponds to a different power and can be adjusted depending on the specific requirement.

Clearly, the above embodiments of the present invention are provided solely for illustrating the examples of the present invention and should not be considered as limitation on the implementation of the invention. For ordinary skilled persons in this field, additional changes or modifications in different forms can be made based on the above description. It is neither necessary nor feasible to exhaustively enumerate all possible embodiments herein. Any modification, equivalent replacement, improvement, or the like made within the spirit and principle of the present invention shall fall within the protection scope of the claims of the present invention.

The invention claimed is:

1. A ventilator, comprising an air supply apparatus, a first servo valve box, a respiratory mask, a signal sensing module, a main control module, and a calibration and learning module; wherein the air supply apparatus is connected to the first servo valve box via a first tubing, and the first servo valve box is connected to the respiratory mask via a second tubing; the air supply apparatus, the first servo valve box, the signal sensing module, and the calibration and learning module are all physically and electrically connected to the main control module; and the first servo valve box at least comprises a first-valve-box main air passage, a first-valve-box branch air passage, and a first servo valve, and the first servo valve is disposed at an exhalation port of the first-valve-box branch air passage; wherein the air supply apparatus is configured to filter air to obtain purified air and convey the purified air along an air passage;

the first servo valve box is configured to receive a first signal sent by the main control module and control the first servo valve to open and close;

the respiratory mask is configured to cover nose or mouth and nose of a user and is provided with an exhaust hole for air exhaustion;

the signal sensing module is configured to acquire a physiological signal feature of the user and feed back the physiological signal feature to the main control module;

the main control module is configured to receive and send a second signal and identify and process the second signal; and the calibration and learning module is configured to learn the physiological signal feature of the user, and the main control module controls an open-close cycle of the first servo valve and controls the air supply apparatus to operate at the preset power;

the signal sensing module comprises an air flow sensor, a pressure sensor, and a signal amplification module, wherein the air flow sensor and the pressure sensor are both electrically connected to the signal amplification module, and the signal amplification module is electrically connected to the main control module; wherein the air flow sensor is close to an inhalation port of the respiratory mask and configured to acquire an air flow change as a respiration signal feature of the user, to obtain an inhalation signal feature, and send the respiration signal feature to the signal amplification module;

the signal amplification module is configured to amplify a third signal sent by the air flow sensor and send an amplified signal to the main control module; and the pressure sensor is configured to acquire fluctuations of a chest and abdominal area of the user as the respiration signal feature of the user, to obtain a chest respiration signal feature and an abdomen respiration signal feature, and send the respiration signal feature to the signal amplification module, wherein a control method of the ventilator is as below, the physiological signal feature of the user is detected and acquired in real time, a respiration type of the user is identified based on the physiological signal feature, when the respiration type is identified as a central sleep apnea type or a mixed sleep apnea type, the ventilator is controlled to provide a continuous-positive-airway-pressure ventilation-system operation mode for the user, and when the respiration type is identified as an obstructive sleep apnea type, a hypopnea type, or a spontaneous respiration type, the ventilator is controlled to provide a pulse operation mode for the user; wherein the physiological signal feature comprises a sleep signal feature and the respiration signal feature, the respiration signal feature comprises the inhalation signal feature, the chest respiration signal feature and the abdomen respiration signal feature, when the inhalation signal feature of the user weakens or disappears, and both the chest respiration signal feature and the abdomen respiration signal feature disappear, the respiration type of the user is determined as the central sleep apnea type;

when the inhalation signal feature of the user weakens or disappears, and the chest respiration signal feature and the abdomen respiration signal feature disappear and then restore but are weak, the respiration type of the user is determined as the mixed sleep apnea type;

when the inhalation signal feature of the user disappears, but the chest respiration signal feature or the abdomen respiration signal feature does not disappear, the respiration type of the user is determined as the obstructive sleep apnea type;

the pulse operation mode is to supply air when the user inhales and to control, when the user exhales, the ventilator to exhaust the supplied air, so as not to supply air to the user, thus supplying air in a pulse manner.

2. The ventilator according to claim 1, wherein the control method of the ventilator comprises following steps:
S1: acquiring, by the signal sensing module, the physiological signal feature of the user in real time;
S2: identifying, by the main control module, the respiration type of the user according to the physiological signal feature, wherein
the respiration type comprises the central sleep apnea type, the mixed sleep apnea type, the obstructive sleep apnea type, the hypopnea type, and the spontaneous respiration type; and
if the current respiration type of the user is the central sleep apnea type or the mixed sleep apnea type, step S3 is performed, and
if the current respiration type of the user is the obstructive sleep apnea type, the hypopnea type, or the spontaneous respiration type, step S4 is performed;
S3: controlling, by the main control module, the air supply apparatus to operate at full power and controlling the first servo valve to close, and returning to step S1;
S4: learning, by the calibration and learning module, the physiological signal feature acquired in step S1, to obtain the drive signal;
S5: controlling, by the main control module, the open-close cycle of the first servo valve according to the drive signal and controlling the air supply apparatus to operate at the preset power; and
S6: completing execution.

3. The ventilator according to claim 2, wherein a power of the air supply apparatus is preset using any one of the following methods:
a first method: determining a ventilation pressure baseline suitable for the user through pressure titration, and presetting the power of the air supply apparatus based on the ventilation pressure baseline; and
a second method: generating a body mass index (BMI) of the user based on height and weight inputted, the BMI being preset with corresponding power, and presetting the power of the air supply apparatus based on the power corresponding to the BMI of the user.

4. The ventilator according to claim 1, wherein the first servo valve box is provided with an inhalation port, a main exhalation port, and a branch exhalation port that form a three-port structure; wherein
the inhalation port of the first servo valve box is connected to an exhalation port of the air supply apparatus via the first tubing, the main exhalation port of the first servo valve box is connected to the inhalation port of the respiratory mask via the second tubing, and the branch exhalation port of the first servo valve box is left open or connected to an inhalation port of the air supply apparatus via a third tubing.

5. The ventilator according to claim 4, wherein the air supply apparatus comprises a fan and an air filter box; wherein an exhalation port of the fan is connected to an inhalation port of the first servo valve box via the first tubing, and an inhalation port of the fan is connected to an exhalation port of the air filter box via a fourth tubing; and the fan is electrically connected to the main control module.

6. The ventilator according to claim 5, wherein when the branch exhalation port of the first servo valve box is connected to the inhalation port of the air supply apparatus via the third tubing, the air supply apparatus further comprises a second servo valve box, wherein the second servo valve box is provided with a main inhalation port, a branch inhalation port, and an exhalation port that form a three-port structure; wherein
the exhalation port of the second servo valve box is connected to an inhalation port of the air filter box via a fifth tubing, and the branch inhalation port of the second servo valve box is connected to the branch exhalation port of the first servo valve box via the third tubing; and the second servo valve box is electrically connected to the main control module; and
the second servo valve box is configured to receive a fourth signal sent by the main control module and control the second servo valve to open and close.

7. The ventilator according to claim 1, further comprising an electroencephalogram sensor and an eye muscle electromyography sensor, wherein the electroencephalogram sensor and the eye muscle electromyography sensor are both electrically connected to the main control module;
the electroencephalogram sensor is configured to acquire an electroencephalogram signal of the user as the sleep signal feature of the user, and send the sleep signal feature to the signal amplification module; and
the eye muscle electromyography sensor is configured to acquire an eye muscle electromyography signal of the user as the sleep signal feature of the user and send the sleep signal feature to the signal amplification module.

\* \* \* \* \*